(12) United States Patent
Rakover et al.

(10) Patent No.: US 10,993,981 B2
(45) Date of Patent: May 4, 2021

(54) COMPOSITIONS FOR TREATMENT OF FOLLICULAR TONSILLITIS USING AN EMULSION BASED ON ROSEMARY EXTRACT AND OREGANO ESSENTIAL OIL

(71) Applicant: THE STATE OF ISRAEL, MINISTRY OF AGRICULTURE & RURAL DEVELOPMENT, AGRICULTURAL RESEARCH ORGANIZATION (ARO), (VOLCANI CENTER), Rishon Lezi (IL)

(72) Inventors: Yoseph Rakover, Kfar Tavor (IL); Nativ Dudai, Kfar Yehezkel (IL)

(73) Assignee: THE STATE OF ISRAEL, MINISTRY OF AGRICULTURE & RURAL DEVELOPMENT, AGRICULTURAL RESEARCH ORGANIATION (ARO), (VOLCANI CENTER), Rishon Lezion (IL)

( * ) Notice: Subject to any disclaimer, the term of this patent is extended or adjusted under 35 U.S.C. 154(b) by 0 days.

(21) Appl. No.: 16/314,781

(22) PCT Filed: Jul. 10, 2017

(86) PCT No.: PCT/IL2017/050775
§ 371 (c)(1),
(2) Date: Jan. 2, 2019

(87) PCT Pub. No.: WO2018/011790
PCT Pub. Date: Jan. 18, 2018

(65) Prior Publication Data
US 2019/0240278 A1    Aug. 8, 2019

Related U.S. Application Data

(60) Provisional application No. 62/360,491, filed on Jul. 11, 2016.

(51) Int. Cl.
| | | |
|---|---|---|
| A61K 36/53 | (2006.01) | |
| A61K 36/537 | (2006.01) | |
| A61P 29/00 | (2006.01) | |
| A61K 9/68 | (2006.01) | |
| A61K 9/00 | (2006.01) | |

(52) U.S. Cl.
CPC .............. *A61K 36/53* (2013.01); *A61K 9/006* (2013.01); *A61K 9/0058* (2013.01); *A61K 36/537* (2013.01); *A61P 29/00* (2018.01)

(58) Field of Classification Search
None
See application file for complete search history.

(56) References Cited

U.S. PATENT DOCUMENTS

| | | | | |
|---|---|---|---|---|
| 5,859,293 A * | 1/1999 | Bailey | ............... | A23L 3/3472 |
| | | | | 562/467 |
| 6,486,203 B1 * | 11/2002 | Dannenberg | ......... | A61K 9/0056 |
| | | | | 514/403 |
| 2006/0134025 A1 * | 6/2006 | Trivedi | ................ | A61K 8/347 |
| | | | | 424/58 |
| 2012/0209026 A1 * | 8/2012 | Wiesmueller | ...... | B01D 11/0203 |
| | | | | 562/466 |
| 2012/0244086 A1 * | 9/2012 | Trivedi | ................ | A61K 8/97 |
| | | | | 424/48 |
| 2018/0250264 A1 * | 9/2018 | Hybertson | ............ | A61P 29/00 |

FOREIGN PATENT DOCUMENTS

| | | |
|---|---|---|
| CN | 1586605 A | 3/2005 |
| CN | 105147971 A | 12/2015 |
| WO | 2011/068811 A1 | 6/2011 |

OTHER PUBLICATIONS

Aruoma O. et al. An Evaluation of the Antioxidant and Antiviral Action of Extracts of Rosemary and Provencal Herbs. Food and Chemical Toxicology 34:449-456, 1996. (Year: 1996).*
Pizzale L. et al. Antioxidant Activity of Sage and Oregano Extracts Related to Their Phenolic Compound Content. J of the Science of Food and Agriculture 82:1645-1651 2002. (Year: 2002).*
International Search Report for PCT/IL017/050775, dated Sep. 19, 2017 (5 pages).
Written Opinion of the International Searching Authority for PCT/IL2017/050775, dated Sep. 19, 2017 (4 pages).
Poeckel et al., "Carnosic acid and carnosol potently inhibit human 5-lipoxygenase and suppress pro-inflammatory responses of stimulated human polymorphonuclear leukocytes", Biochemcial Pharmacology 76 (2008) 91-97 (7 pages).
European Medicines Agency, Committee of Herbal Medicinal Products, "Assessment report on *Salvia officinalis* L., folium and *Salvia othcinalis* L., aetheroleum", Feb. 2, 2016 (44 pages).
Julien Sfeir et al., "In Vitro Antibacterial Activity of Essential Oils against *Streptococcus pyogenes*", Evidence-Based Complementary and Alternative Medicine, vol. 2013, (2013) (10 pages).
Suter et al., "Results of all scientific investigations with the A.Vogel Sore Throat Spray", Issue 2—Jun. 2008 (12 pages).

* cited by examiner

*Primary Examiner* — Ralph J Gitomer
(74) *Attorney, Agent, or Firm* — Roach Brown McCarthy & Gruber P.C.; Kevin D. McCarthy

(57) ABSTRACT

A composition for the treatment of follicular tonsillitis is provided. The composition includes a therapeutically effective amount of carnosic acid and a carrier consisting of pharmaceutically acceptable solvents and ingredients. The composition is in the form of spray and includes ethanol and polyoxyethylenesorbitan monooleate and at least 0.1% oregano essential oil. Other compositions and treatment methods are disclosed.

8 Claims, No Drawings

COMPOSITIONS FOR TREATMENT OF FOLLICULAR TONSILLITIS USING AN EMULSION BASED ON ROSEMARY EXTRACT AND OREGANO ESSENTIAL OIL

BACKGROUND OF THE INVENTION

The present invention relates to the field of pharmaceutics and more particularly, to compositions comprising carnosic acid for the treatment of follicular tonsillitis.

Carnosic acid is a diterpene occurring in a number of plants, such as rosemary (*Rosmarinus officinalis*) and sage (*Salvia officinalis*), especially in the leaves. Other diterpenes occurring in these plants are 12-O-methyl carnosic acid, carnosol, rosmanol, isorosmanol and 11, 12-di-O-methyl-isorosmanol.

The isolation of the actives from the above mentioned plants may be done by several methods, the best known of which are steam distillation (leading to essential oils) and extraction (leading to extracts).

Essential oils and extracts have very different compositions because, while the essential oils contain the volatile compounds in the plant, the extracts contain the compounds soluble in the extracting solvent or medium.

As carnosic acid is a polar compound, it is not expected to be volatile, therefore its presence in the essential oils, if any, is expected to be very low.

The plant leaves extraction may be carried out with a solvent or mixture of solvents, aqueous or non-aqueous, or by supercritical extraction. The solvent, temperature, pH, ratios and other conditions affect the extract's composition. The extraction may be followed by a concentration step, in which a concentrate is obtained which is enriched in one or more actives. The concentrate contains a relatively high percentage of carnosic acid and other components extracted side-by-side with it.

Carnosic acid has been shown to have some beneficial medical effects.

SUMMARY OF THE INVENTION

The present invention deals with carnosic acid extracts, fractions and concentrates of plant origin, obtained by an extraction process, in contrast to essential oils, obtained by distillation.

It is an object of this invention to provide compositions comprising carnosic acid for the treatment of follicular tonsillitis.

The carnosic acid in said compositions is of botanical origin and is obtained by an extraction process from the leaves of certain carnosic acid containing plants, especially rosemary and sage. After the extraction, the extract is further processed to obtain carnosic acid fractions and concentrates of relatively high concentrations.

Methods of treatment of *streptococcus* infections and follicular tonsillitis with the compositions of this invention are also provided.

DETAILED DESCRIPTION OF THE INVENTION

The wording herein below is implied in the common meaning of the definitions and statements as known to the versed in the art of pharmaceuticals and polymer science.

As used in the specification and claims, the forms "a", "an" and "the" include singular as well as plural references unless the context clearly dictates otherwise.

Further, as used herein, the term "comprising" is intended to mean that the system includes the recited elements, but not excluding others which may be optional in the design of the system, such as fillers and the like. The term "consisting essentially of" is used to define a system that includes the recited elements but exclude other elements that may have an essential significance effect on the performance of the system. "Consisting of" shall thus mean excluding more than traces of other elements.

"Extract" or "herbal extract" or "plant extract" is a mixture extracted from plant or herbal parts by an extraction process using a solvent or solvent mixture. In the context of the instant invention, "extract" denotes the raw extract or a fraction or concentrate obtained from the extract.

"Essential oil" also known as "ethereal oil" or "volatile oil" is a concentrated hydrophobic liquid usually obtained from plants or herbs by distillation, or steam distillation.

"Concentrate" in the context of the instant invention means the residue obtained from an extract after most or all of the solvent removed.

"Fraction" in the context of the instant invention means a part of an extract or an essential oil, obtained by separation using any physical method.

This invention provides methods of treatment and compositions for the treatment of follicular tonsillitis.

Tonsillitis is an infection of the palatine tonsils, which may be acute, subacute or chronic. Palatine tonsils consist of an extensive system of crypts (follicles). The tonsillar follicles are sometimes invaded by bacteria or viruses, causing an inflammation of the mucous membrane covering the tonsils and lining the follicles, a condition known as follicular tonsillitis. Mosby's Medical Dictionary, $8^{th}$ Ed. 2009 defines follicular tonsillitis as "an inflammation of the tonsils accompanied by a purulent infection of the tonsillar crypts". Viral infection with secondary bacterial invasion may be one mechanism of the disease initiation. While Group A beta-hemolytic *streptococci* (GABHS) are the most common pathogens involved in the pathology of tonsillitis, other pathogens, such as anaerobic bacteria (Brook I. Et al, "The role of anaerobic bacteria in Tonsillitis", Int. J. Pediatr. Otorhinolaryngology, 69(1); 9-19, 2005, January) and viruses are involved as well.

While follicular tonsillitis treatments are known in the art, the hitherto available treatments suffer from several drawbacks.

Follicular tonsillitis is treated with a number of drugs, homeopathic and folkloric preparations, but mostly with antibiotics. Extensive use of antibiotics should be avoided (see "Overuse of antibiotics with upper respiratory tract infections in a primary care clinic" Cohen A. D. et al. Harefuah, 2001 September; 140(9); 810-2, 896).

The antimicrobial activity of 52 essential oils and other plant extracts has been investigated in an extensive study ("Antimicrobial activity of essential oils and other plant extracts" K. A. Hammer et al, J. of Appl. Microbiol. 1999, 86, 985990) against 10 pathogens, but not against *streptococcus*. In this study, the *Rosmarinus officinalis*, known to have a high carnosic acid content was included but only its essential oil was studied, not the extracts. Again, due to the polar nature of carnosic acid, it is expected to be found in the extracts not in the essential oils.

*Rosmarinus* extracts were used to treat *Streptococcus iniae* in tilapia fish ("Use of *Rosmarinus officinalis* as a treatment against *Streptococcus* iniae in tilapia, *Oreochromis* sp.", S. Abutbul et al., Aquaculture 238 (2004) 97-105), but not in humans.

Rosemary, sage and other medicinal plants contain a very large number of compounds, and the plant isolates (essential oils or extracts) vary greatly in their composition. So, there is no telling which of the multiple compounds in the isolates is responsible for the therapeutic effect, if any.

The instant invention singles out carnosic acid as the main therapeutically effective plant component, and provides compositions of known and well-defined carnosic acid content. Other components of the plant extracts may have beneficial therapeutic effects, either additive or synergistic or stabilizing or antioxidant effects. The active used in the compositions of the instant invention is a plant extract, concentrate or fraction comprising carnosic acid in relatively high concentrations but also other compounds extracted from the plants alongside carnosic acid.

There is an unmet need in the art for efficient methods of treatment of follicular tonsillitis with well-defined preparations of botanical origin.

While treatments with botanical preparations are sometimes effective, the composition of the botanical preparations is largely unknown and large variations in their composition are expected due to the geographical origin, crop season, genotype, botanical subspecies, etc.

The instant invention provides for compositions having a well-defined content of the active carnosic acid as extract of botanical origin. The botanical compositions of this invention enable efficient and reproducible treatment of follicular tonsillitis, while avoiding the use of traditional antibiotics. Therefore, the compositions of this invention, having a reproducible content of the active, are expected to result in a reproducible therapeutic effect. In addition, the reproducible carnosic acid content allows for reliable dose-response studies.

The instant invention provides tools for a simple and efficient treatment of follicular tonsillitis with compositions comprising carnosic acid extracted from botanical sources.

In one embodiment, there are provided compositions for the treatment of follicular tonsillitis, comprising a therapeutically effective amount of carnosic acid and a carrier consisting of pharmaceutically acceptable solvents and ingredients.

The carnosic acid in said composition is a component of a plant extract or a concentrate or fraction thereof.

The carnosic acid extract or concentrate or fraction may be obtained from a carnosic acid containing plant such as rosemary (*Rosmarinus officinalis*) or sage (*Salvia officinalis*) The extraction is carried out on the leaves of the carnosic acid containing plants. Rosemary is the preferred source of carnosic acid.

The carnosic acid concentrate described in the examples of this invention is of commercial source (VivOX® 40 from the company Vitiva d.d.-Slovenia) extracted from rosemary leaves, having a carnosic acid content of >40% (HPLC). VivOX® is a yellow to brown powder, having a water content of less than 2% and being soluble in oil or ethanol. VivOX® is GRAS (Generally Recognized As Safe) certified by the FDA 21 CFR 182.10 and is classified as a flavor by Council Directive 88/388/EEC.

In another embodiment, the compositions of this invention further comprise at least one additional plant extract or essential oil in addition to the carnosic acid extract.

The additional essential oil may originate from Lamiaceae plants such as *Origanum syriacum* (oregano).

In a preferred embodiment, there are provided compositions for the treatment of follicular tonsillitis, comprising a therapeutically effective amount of carnosic acid, optionally an additional essential oil originating for example from Lamiaceae plants such as *Origanum syriacum* (oregano) and a carrier consisting of pharmaceutically acceptable solvents and ingredients. The preferred solvent for solubilizing the carnosic acid concentrate is ethanol, and the compositions' carrier is preferably water.

Carnosic acid in the above compositions is a component of a plant extract or a concentrate or fraction thereof.

The plant extract is obtained by extraction of the leaves of a plant selected from the group comprising rosemary (*Rosmarinus officinalis*), sage (*Salvia officinalis*) and other plants. The preferred plant source is rosemary leaves, but other sources may be used as well.

The plant extract may be optionally further processed, to afford a concentrate or a fraction of higher, and well-defined carnosic acid content.

The compositions of this invention comprise between 0.1% and 2.0% carnosic acid, preferably between 0.5% and 1.5%, more preferably between 0.6% and 1.0% and most preferably 0.8% carnosic acid.

The administration of the compositions of this invention may be done in a pharmaceutically acceptable dosage form, selected from spray, nasal spray, lotion, lozenge, tablet, capsule, drops, chewing gum, tincture and throat wash.

The preparation process of the carnosic acid containing compositions includes dissolution of a carnosic acid extract or concentrate or fraction in a suitable solvent (such as ethanol), addition of other ingredients, such as surfactants (such as Tween® which is a commonly referred to as polyoxyethylenesorbitan monooleate), stabilizers, antioxidants, sequestering agents, buffers, etc and dilution in the water carrier.

The composition may comprise between 0.1% and 5% of a rosemary extract having a 40% carnosic acid content, between 2% and 10% ethanol, between 5% and 12% Tween®, other pharmaceutically acceptable ingredients according to need, and between 60% and 95% water.

Preferably, the compositions comprise between 1-3% of a rosemary extract having a 30-50% carnosic acid content, and more preferably 2% of an extract having about 40% carnosic acid content.

In a preferred embodiment, the carnosic acid composition is administered as a spray comprising 2% of a rosemary extract having a 40% carnosic acid content, 5% ethanol, 8% Tween® and 85% water.

There is provided a composition of this invention in the form of spray or aerosol, whenever administered to a patient in need thereof as 2-20 puffs daily.

The instant invention provides also a method of treatment of follicular tonsillitis by the daily administration, optionally preceded by a priming treatment, to a patient in need thereof of one or more dosage units of a pharmaceutically acceptable dosage form, selected from spray, nasal spray, lotion, lozenge, tablet, capsule, drops, chewing gum, tincture and throat wash.

A method of treatment for patients which complain of throat pain and are diagnosed with follicular tonsillitis is provided, employing the compositions of the instant invention (Example 3). The treatment may be in the form of spray (see Example 1), wherein each puff is about 0.1 ml of solution. At the beginning of the treatment, the volunteers were given a priming spray dose of 4 puffs every 5 minutes—that is 16 puffs over 20 minutes. The treatment was continued for 10 consecutive days, with three treatments per day: morning, noon and evening. Every treatment included 4 puffs into the throat, that was 12 puffs per day and 120 puffs over the whole 10 days period.

A method of treatment for patients who are found to be positive carriers of *Streptococcus pyogenes* (but not diagnosed with follicular tonsillitis) is also provided (Example 4), employing the compositions of the instant invention. Six positive volunteers were treated with a spray containing volatile aromatic oils obtained from *Origanum syriacum* and *Rosmarinus officinalis* (Example 2). The spray was administered locally to the buccal cavity around the tonsils using a spray dispenser. The treatment included a priming dosage whereby each volunteer was administered 16 puffs over 20 minutes, followed by a daily dosage whereby each volunteer was given 12 puffs daily for 10 days—total of 120 puffs. Four throat culture samples were collected from each volunteer at different times before, during and at the end of the treatment. At the end of the above 10 days treatment, 4 out of the 5 participating volunteers had negative throat culture, and only one had positive throat culture. No adverse effects were observed during the treatment.

The results were very positive, in light of the fact that the classical antibiotic treatment of severe streptococcal throat infections fails to cure the infection in 35% of the cases (Sela, S., and Barzilai, A. Why do we fail with penicillin in the treatment of group a *streptococcus* infection? Ann. of Med. 31: 303-307; 1999).

Therefore, the compositions of this invention open new avenues in the treatment of streptococcal throat infections.

In a preferred embodiment, the compositions of this invention are applied for 1-8 times per day as a spray, each time 4 puffs, for 3-15 consecutive days, preferably 4 times a day for 10 days or 2-20 puffs a day for about 10 days after a priming dosage.

In another embodiment, there is provided a method of treatment of follicular tonsillitis by the daily administration to a patient in need thereof of one or more dosage units of one of the compositions of this invention, wherein the treatment is continued for 2-15 days.

In yet another embodiment, there is provided a method of treatment of streptococcal throat infections by administration to a patient in need thereof of a priming dose of 8-20 puffs, followed by 2-20 daily puffs of one of the compositions of this invention, wherein the treatment is continued for 2-15 days.

The dosage forms of this invention may be dispensed as a kit including a number of unit dosage forms and instructions for the use of the kit.

EXAMPLES

The following examples further illustrate the invention as it may be carried out but, of course, should not be construed as in any way limiting its scope.

Materials

The carnosic acid extract described in the examples is VivOX, a commercial rosemary leaves extract product obtained from Vitiva d.d.-Slovenia, having a >40% (HPLC) carnosic acid content.

Tween® 80 (Polysorbate 80) is a commercial product from Sigma Aldrich.

Example 1

Dissolve 2 grams of VivOX® with a 40% carnosic acid content in 5 ml of ethanol 95%. Add to the solution 8 ml of Tween® 80 and stir until dissolution. Dilute the obtained solution with about 85 ml distilled water, to afford 100 grams of carnosic acid composition with 0.8% carnosic acid content. Fill the composition in 20 ml spray bottles.

Example 2

Dissolve 2 grams of VivOX® with a 40% carnosic acid content and 0.1 ml *Origanum syriacum* (oregano) essential oil in 5 ml of ethanol 95%. Add to the solution 8 ml of Tween® 80 and stir until dissolution. Dilute the obtained solution with about 85 ml distilled water, to afford 100 grams of carnosic acid containing composition with 0.8% carnosic acid content. Fill the composition in 20 ml spray bottles.

Example 3

Fifty adult volunteers older than 18 years were selected, which complain of throat pain and were diagnosed with follicular tonsillitis less than 48 hours prior to inclusion, and had given informed consent. Exclusion criteria: the volunteers were not anesthetized with tubus for two months before the study. Following signing informed consent, patients were asked to participate in a baseline evaluation that included physician's clinical assessment, throat culture, and record of demographics.

The treatment was given in the form of spray (see Example 1), wherein each puff is about 0.1 ml of solution.

At the beginning of the treatment, the volunteers were given a priming spray dose of 4 puffs every 5 minutes—that is 16 puffs over 20 minutes.

The treatment was continued for 10 consecutive days, with three treatments per day: morning, noon and evening. Every treatment included 4 puffs into the throat, that is 12 puffs per day and 120 puffs over the whole 10 days period.

Example 4

Seventy three adult volunteers aged above 18 were tested for presence of *Streptococcus pyogenes* in the buccal cavity.

Six volunteers out the 73 candidates were found positive carriers and, after signing confirmed consent, were enrolled for the study. One of the positive volunteers did not report for control and was not included in the study.

The volunteers were treated with a spray containing volatile aromatic oils obtained from *Origanum syriacum* and *Rosmarinus officinalis* as described in example 2. The spray was administered locally to the buccal cavity around the tonsils using a spray dispenser.

The treatment included:

Priming dosage: each volunteer was administered 16 puffs over 20 minutes.

Daily dosage: each volunteer was given 12 puffs daily for 10 days—total of 120 puffs.

Sampling: 4 throat culture samples were collected from each volunteer: Before treatment After 3-5 days After 6-8 days End of treatment—9-11 days Results:

At the end of the above 10 days treatment, 4 out of the 5 participating volunteers had negative throat culture, and only one had positive throat culture. No adverse effects were observed during the treatment.

The invention claimed is:

1. A composition for the treatment of follicular tonsillitis, the composition consisting of:

a therapeutically effective amount of carnosic acid provided as between 0.1% and 5% of a rosemary extract having a 40% carnosic acid content;

a carrier consisting of between 2% and 10% ethanol, between 5% and 12% surfactant and between 70% and 95% water; and at least 0.1% oregano essential oil;

wherein said composition is an emulsion.

2. The composition of claim 1, wherein said surfactant is polyoxyethylenesorbitan monooleate.

3. The composition of claim 1, comprising between 0.1% and 2.0% carnosic acid.

4. The composition of claim 1, less than 0.5% oregano essential oil.

5. The composition of claim 1, comprising 2% of a rosemary extract.

6. A method comprising:

administering to a subject with follicular tonsillitis a composition according to claim 1 locally on the tonsils.

7. The method of claim 6, wherein said administering includes spraying.

8. A composition according to claim 1 provided in a dosage form selected from the group consisting of a spray, a nasal spray, a lotion, a lozenge, drops, chewing gum, a tincture and a throat wash.

\* \* \* \* \*